United States Patent
Levorse, Jr. et al.

(10) Patent No.: US 7,265,231 B2
(45) Date of Patent: Sep. 4, 2007

(54) 3-METHYL OXETANEMETHANOL DERIVATIVES AND THEIR USE IN PERFUME COMPOSITIONS

(75) Inventors: Anthony T. Levorse, Jr., Westfield, NJ (US); Gary Mertz, Freehold, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 112 days.

(21) Appl. No.: 11/105,625

(22) Filed: Apr. 14, 2005

(65) Prior Publication Data

US 2006/0234882 A1    Oct. 19, 2006

(51) Int. Cl.
*C07D 305/00* (2006.01)

(52) U.S. Cl. .................................... 549/510

(58) Field of Classification Search ................ 549/510, 549/511

See application file for complete search history.

(56) References Cited

U.S. PATENT DOCUMENTS

| 2,854,486 | A |   | 9/1958 | McShane, Jr. |         |
|-----------|---|---|--------|--------------|---------|
| 2,924,607 | A | * | 2/1960 | Pattison     | 549/510 |
| 6,753,434 | B1| * | 6/2004 | Musa         | 549/510 |

* cited by examiner

*Primary Examiner*—D. Margaret Seaman
*Assistant Examiner*—Nizal S. Chandrakumar
(74) *Attorney, Agent, or Firm*—Elizabeth M. Quirk

(57) ABSTRACT

The present invention relates to new 3-methyl oxetanemethanol derivatives and their use as fragrance chemicals suitable for incorporation in fine fragrances, cosmetics, toiletries and related applications.

2 Claims, No Drawings

3-METHYL OXETANEMETHANOL DERIVATIVES AND THEIR USE IN PERFUME COMPOSITIONS

FIELD OF THE INVENTION

The present invention relates to new 3-methyl oxetanemethanol derivatives and their use as fragrance chemicals suitable for incorporation in fine fragrances, cosmetics, toiletries and related applications.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances. The preparation of the compound 3-methyl oxetanemethanol is disclosed by Pattison (J. Amer. Chem. Soc., 79, p3455, 1957).

SUMMARY OF THE INVENTION

The present invention provides novel chemicals, and the use of the chemicals to enhance the fragrance of perfumes, toilet waters, colognes, personal products and the like. More specifically, the present invention is directed to the novel compounds represented by the general structure of the Formula I set forth below:

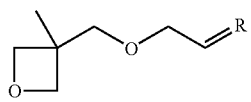

Formula I wherein R is selected from the group consisting of straight, branched, cyclic or aromatic hydrocarbon moieties containing single and/or double bonds; carbonyls and carboxy compounds.

In another embodiment, the present invention is directed to a method for enhancing a perfume by incorporating an olfactory acceptable amount of compounds represented by the general structure of the Formula II set forth below:

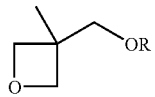

Formula II wherein R is selected from the group consisting of straight, branched, cyclic or aromatic hydrocarbon moieties containing single and/or double bonds; carbonyls and carboxy compounds.

These and other embodiments of the present invention will be apparent by reading the following specification.

DETAILED DESCRIPTION OF THE INVENTION

In the Formulae I and II above R is selected from the group consisting of straight, branched, cyclic or aromatic hydrocarbon moieties containing single and/or double bonds; carbonyls and carboxy compounds.

Suitable straight hydrocarbon moieties include ethyl, propyl, butyl, cyclopentyl, cyclohexyl, and the like. Suitable branched hydrocarbon moieties include isopropyl, sec-butyl, tert-butyl, 2-ethyl-propyl, and the like. Suitable hydrocarbon moieties containing double and triple bonds include ethene, propene, 1-butene, 2-butene, penta-1-3-deine, hepta-1,3,5-triene, butyne, hex-1-yne and the like. Suitable cyclic hydrocarbon moieties include cyclopropyl, cyclobutyl, cyclopentyl, cyclohexyl and the like. Suitable aromatic moieties include phenyl, benzyl, phenylethyl and the like. Suitable carbonyls include derivatives of aldehydes such as formaldehyde, acetaldehyde, propionaldehyde, butyraldehyde, benxaldehyde and the like; derivatives of ketones such as acetone, methyl ethyl ketone, methyl n-propyl ketone, diethyl ketone, 2-hexanone, 3-hexanone and the like.

In the preferred embodiment of the invention, the novel compounds of the present invention are represented by the following structures:

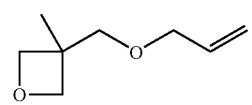

Formula III

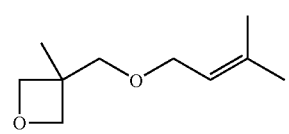

Formula IV

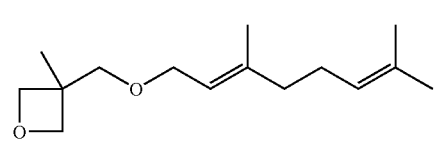

Formula V

Those with the skill in the art will appreciate that the compound of Formula III is 3-methyl-3-[(2-propenyloxy)methyl] oxetane, the compound of Formula IV is 3-methyl-3-[(3-methylbutyl)oxy]methyl oxetane, the compound of Formula V is 3,7-dimethyl-1-[(3-methyloxetane-3yl)methyloxy]octa-2,6-diene.

The table below lists additional compounds derived from Formula I that are described in the present invention:

| R | Compound |
|---|---|
| $C(CH_3)C_3H_7$ | 3-methyl-3-(3-methyl-hex-2-ethyloxymethyl)oxetane |
| $C(CH_3)C_4H_9$ | 3-methyl-3-(3-methyl-hept-2-ethyloxymethyl)oxetane |
| $C(CH_3)C_4H_8$ | 3-methyl-3-(3-methyl-hepta-2,6-dienyloxymethyl)oxetane |
| $C(CH_3)C_2H_4CHC_2H_4$ | 3-(5-Cyclopropyl-3-methyl-pent-2-enyloxymethyl)-3-methyl-oxetane |
| $C(CH_3)$Phenyl | 3-(3-cyclohexyl-but-2-enyloxymethyl)-3-methyl-oxetane |
| $C(CH_3)CN$ | 2-methyl-4-(3-methyl-oxetan-3-ylmethoxy)-but-2-enenitrile |

-continued

| R | Compound |
|---|---|
| C(CH$_3$)COCH$_3$ | 3-methyl-5-(3-methyl-oxetan-3-ylmethoxy)-pent-3-en-2-one |
| C(CH$_3$)COC$_3$H$_7$ | 3-methyl-1-(3-methyl-oxetan-3-ylmethoxy)-hept-2-en-4-one |
| C(CH$_3$)COC$_3$H$_6$ | 5-methyl-7-(3-methyl-oxetan-3-ylmethoxy)-hepta-1,5-dien-4-one |
| C(CH$_3$)COCH$_2$CHC$_2$H$_4$ | 1-cyclopropyl-3-methyl-5-(3-methyl-oxetan-3-ylmethoxy)-pent-3-en-2-one |

With reference to the compounds of our invention, the synthesis is effected by means of the reaction of 3-methyl oxetanemethanol with methyl ether under sodium methoxide catalysis to furnish the desired compound according to the scheme below:

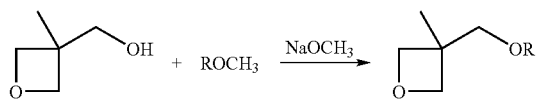

base is added to a mixture of the 3-methyl oxetanemethanol and an ester which is then heated at a temperature ranging from 60° C. to 150° C., most preferably from 90° C. to 120° C. Methanol is distilled overhead and removed from the reaction. The mixture is cooled to 25° C. and neutralized with acetic acid. The reaction mass is given a 10% aqueous sodium chloride solution wash and the crude product is purified by distillation. The reaction occurs in 70-90% mole yield based on ester, methyl benzoate. The preparation of the compound 3-methyl oxetanemethanol is disclosed by Pattison (J. Amer. Chem. Soc., 79, p3455, 1957).

In another embodiment, the present invention is directed to a method for enhancing a perfume by incorporating an olfactory acceptable amount of compounds represented by the general structure of the Formula II set forth below:

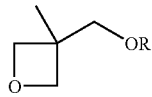

Formula II wherein R is selected from the group consisting of straight, branched, cyclic or aromatic hydrocarbon moieties containing single and/or double bonds; carbonyls and carboxy compounds.

Suitable straight hydrocarbon moieties include ethyl, propyl, butyl, cyclopentyl, cyclohexyl, and the like. Suitable branched hydrocarbon moieties include isopropyl, sec-butyl, tert-butyl, 2-ethyl-propyl, and the like. Suitable hydrocarbon moieties containing double and triple bonds include ethene, propene, 1-butene, 2-butene, penta-1-3-deine, hepta-1,3,5-triene, butyne, hex-1-yne and the like. Suitable cyclic hydrocarbon moieties include cyclopropyl, cyclobutyl, cyclopentyl, cyclohexyl and the like. Suitable aromatic moieties include phenyl, benzyl, phenylethyl and the like. Suitable carbonyls include derivatives of aldehydes such as formaldehyde, acetaldehyde, propionaldehyde, butyraldehyde, benxaldehyde and the like; derivatives of ketones such as acetone, methyl ethyl ketone, methyl n-propyl ketone, diethyl ketone, 2-hexanone, 3-hexanone and the like.

The table below lists some of the compounds derived from Formula II that are described in the present invention:

| R | Compound |
|---|---|
| C$_2$H$_5$ | 3-Ethoxymethyl-3-methyl-oxetane |
| C$_2$H$_4$ | 3-methyl-3-vinyloxymethyl-oxetane |
| CH$_2$CH(CH$_3$)$_2$ | 3-isobutoxymethyl-3-methyl-oxetane |
| COCH$_3$ | (3-methyloxetan-3-yl)methyl 2 methylacetate |
| COCH$_2$CH$_2$CH$_3$ | (3-methyloxetan-3-yl)methyl 2 methylpropanoate |
| COCH$_2$CH$_2$CH$_2$CH$_3$ | (3-methyloxetan-3-yl)methyl 2 methylbutanoate |
| COCH$_2$CH$_2$CH$_2$CH$_2$CH$_3$ | (3-methyloxetan-3-yl)methyl 2 methylpentanoate |
| COOCH$_3$ | Ethyl 2-(3-methyloxetane-3-yloxy)acetate |
| COOCH$_2$CH$_2$CH$_3$ | Ethyl 2-(3-methyloxetane-3-yloxy)propanoate |
| COO(CH$_2$)$_6$CH$_3$ | Ethyl 2-(3-methyloxetane-3-yloxy)heptanoate |

The synthesis of these compounds is described in the examples below.

The use of this compound is widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, dishwashing materials, scrubbing compositions, window cleaners, and the like.

In these preparations, the compound of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry,. raspberry; musk, flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8 and most preferably from about 0.5 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

The following are provided as specific embodiments of the present invention. Other modifications of this invention will be readily apparent to those skilled in the art; without departing from the scope of this invention. As used herein all percentages are weight percent. IFF is meant to be understood as International Flavors & Fragrances Inc.

EXAMPLE 1 PREPARATION OF ESTERS OF THE PRESENT INVENTION

The following reaction sequence was used to prepare the specific compounds described by the NMR data set forth below:

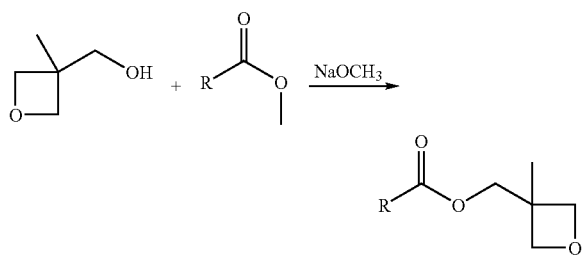

The 3-methyl oxetanemethanol (1.3 mole) and ester (1 mole) are combined to which sodium methoxide (0.2 mole) is added. The resulting mixture is heated to 90° C. to 120° C., and methanol is removed from the reaction via a Dean-Stark trap. The reaction is aged until methanol is no longer produced and GC analysis of the reaction indicates less than 10% starting ester is present. The reaction mass is cooled to room temperature and neutralized with acetic acid (0.5 mole). The reaction is washed with 10% aqueous sodium chloride solution. The crude reaction mass is purified by fractional distillation affording the product ester.

The esters are synthesized according to the general scheme above with the following specific examples. Equivalents set out are mole equivalents based on starting esters, yields are distilled chemical yields based on starting ester.

(3-methyloxetan-3-yl)methyl 2-methylpropanoate 3-methyloxetane methanol 1.3eq, methyl 2-methylpropanoate 1eq, sodium methoxide 0.2eq, quench, acetic acid 0.5eq, with 10% sodium chloride solution, yield=88%. Odor: fruity.

1.20 ppm (d, 6H, J=7.01 Hz) 1.34 ppm (s, 3H) 2.61 ppm (septet, 1H, J=6.99 Hz) 4.16 ppm (s, 2H, d) 4.38 ppm (d, 2H, J=5.93 Hz) 4.53 ppm (d, 2H, J=5.93 Hz)

(3-methyloxetan-3-yl)methyl 2-methylpentanoate 3-methyloxetane methanol 1.3eq, methyl. 2-methylpentanoate 1eq, sodium methoxide 0.2eq, quench, acetic acid 0.5eq, with 10% sodium chloride solution, yield=80%. Odor: fruity apple like.

0.91 ppm (t, 3H, J=7.21 Hz) 1.17 ppm (d, 3H, J=7.00 Hz) 1.32 ppm (m, 1H) 1.34 ppm (s, 3H) 1.36 ppm (m, 2H) 1.66 ppm (m, 1H) 2.51 ppm (sextet, 1H, J=6.95 Hz) 4.16 ppm (s, 2H) 4.38 ppm (d, 2H, J=5.94 Hz) 4.53 ppm (d, 2H, J=5.92 Hz)

(3-methyloxetan-3-yl)methyl 3-methylbutanoate 3-methyloxetane methanol 1.3eq, methyl 3-methylbutanoate 1eq, sodium methoxide 0.2eq, quench, acetic acid 0.5eq, with 10% sodium chloride solution, yield=90%. Odor: fruity tropical like.

0.97 ppm (d, 6H, J=6.62 Hz) 1.34 ppm (s, 3H) 2.12 ppm (m, 1H) 2.25 ppm (d, 2H, J=7.30 Hz) 4.17 ppm (s, 2H) 4.38 ppm (d, 2H, J=5.95 Hz) 4.52 ppm (d, 2H, J=5.95 Hz)

(3-methyloxetan-3-yl)methyl (6E)-3,7-dimethyloct-6-enoate 3-methyloxetane methanol 1.3eq, methyl (6E)-3,7-dimethyloct-6-enoate 1eq, sodium methoxide 0.2eq, quench, acetic acid 0.5eq, with 10% sodium chloride solution, yield=86%. Odor: weak fruity.

0.96 ppm (d, 3H, J=6.64 Hz) 1.09-1.31 ppm (m, 1H) 1.34 ppm (s, 4H) 1.60 ppm (s, 3H) 1.68 ppm (s, 3H) 1.93-2.07 ppm (m, 3H) 2.18 ppm (d, 1H, J=14.69 Hz, of d, J=8.13 Hz) 2.37 ppm (d, 1H, J=14.69 Hz, of d, J=6.00 Hz) 4.17 ppm (s, 2H) 4.38 ppm (d, 2H, J=5.94 Hz) 4.52 ppm (d, 2H, J=5.94 Hz) 5.08 ppm (t, 1H, J=7.10 Hz)

(3-methyloxetan-3-yl)methyl octanoate 3-methyloxetane methanol 1.3eq, methyl octanoate 1eq, sodium methoxide 0.2eq, quench, acetic acid 0.5eq, with 10% sodium chloride solution, yield = 90%. Odor: weak woody like.

0.88 ppm (t, 3H, J=6.85 Hz) 1.27-1.32 ppm (m, 8H) 1.34 ppm (s, 3H) 1.64 ppm (pentet, 2H, J=7.38 Hz) 2.36 ppm (t, 2H, J=7.54 Hz) 4.16 ppm (s, 2H) 4.39 ppm (d, 2H, J=5.94 Hz) 4.52 ppm (d, 2H, J=5.93 Hz)

The following 3-methyl oxetanremethanol esters are prepared as cited in references provided.

Kanoh, S; Naka, M; Nishimura, T; Motoi, M, Tetrahedron 58, 7049-64, 2002.

Rakus, K; Verevkin, S; Peng, W; Beckhous, H; Ruchardt, C, Liebigs Ann. Org. Bioorg. Chem. 12, 2059-68, 1995.

Dale, J; Fredriksen, S, Acta Chemica Scandinavica 45, 82-91, 1991.

Corey, E; Natarajan, R, Tetrahedron Lett. P5571-5574, 1983.

(3-methyloxetan-3-yl)methyl hexanoate

Odor: sour acidic.

0.90 ppm (t, 3H, J=6.95 Hz) 1.31-1.33 ppm (m, 4H) 1.34 ppm (s, 3H) 1.65 ppm (pentet, 2H, J=7.44 Hz) 2.36 ppm (t, 2H, J=7.54 Hz) 4.16 ppm (s, 2H) 4.38 ppm (d, 2H, J=5.92 Hz) 4.52 ppm (d, 2H, J=5.91 Hz)

(3-methyloxetan-3-yl)methyl benzoate

Odor: non descript.

1.42 ppm (s, 3H) 4.39 ppm (s, 2H) 4.45 ppm (d, 2H, J=5.93 Hz) 4.64 ppm (d, 2H, J=5.93 Hz) 7.46 ppm (t, 2H, J=7.82 Hz) 7.56 ppm (t, 1H, J=7.42 Hz) 8.07 ppm (d, 2H, J=7.77 Hz)

(3-methyloxetan-3-yl)methyl acetate

Odor: fruity strawberry like.

1.34 ppm (s, 3H) 2.10 ppm (s, 3H) 4.16 ppm (s, 2H,) 4.37 ppm (d, 2H, J=5.94 Hz) 4.51 ppm (d, 2H, J=5.94 Hz)

(3-methyloxetan-3-yl)methyl propanoate

Odor: fruity like.

1.17 ppm (t, 3H, J=7.57 Hz). 1.34 ppm (s, 3H) 2.39 ppm (q, 1H, J=7.58 Hz) 4.17 ppm (s, 2H) 4.38 ppm (d, 2H, J=5.94 Hz) 4.52 ppm (d, 2H, J=5.94 Hz)

(3-methyloxetan-3-yl)methyl heptanoate

Odor: fruity pineapple like.

0.89 ppm (t, 3H, J=6.79 Hz) 1.30 ppm (s, 3H) 1.34 ppm (s, 6H) 1.64 ppm (m, 2H) 2.36 ppm (t, 2H, J=7.52 Hz) 4.16 ppm (s, 2H) 4.38 ppm (d, 2H, J=5.94 Hz) 4.52 ppm (d, 2H, J=5.94 Hz)

(3-methyloxetan-3-yl)methyl butyrate

Odor: fruity like.

0.97 ppm (t, 3H, J=7.42 Hz) 1.34 ppm (s, 3H) 1.68 ppm (sextet, 2H, J=7.32 Hz) 2.34 ppm (t, 2H, J=7.41 Hz) 4.17 ppm (s, 2H) 4.38 ppm (d, 2H, J=5.95 Hz) 4.52 ppm (d, 2H, J=5.96 Hz)

3-methyl-but-2-enoic acid 3-methyloxetan-3-yl methyl ester

Odor: green metallic like.

1.35 ppm (s, 3H) 1.92 ppm (d, 3H, J=1.32 Hz) 2.18 ppm (d, 3H, J=1.26 Hz) 4.17 ppm (s, 2H) 4.38 ppm (d, 2H, J=5.92 Hz) 4.54 ppm (d, 2H, J=5.93 Hz) 5.73 ppm (t, 1H, J=1.32 Hz)

EXAMPLE 2 PREPARATION OF ETHERS OF THE PRESENT INVENTION

The following reaction sequence was used to prepare the specific compounds described by the NMR data set forth below:

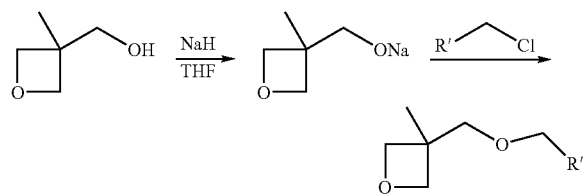

The 3-methyl oxetanemethanol (1 mole) is dissolved in THF (500 mL) and fed into 60% sodium hydride dispersion (1.1 mole) in THF (500 mL) at 0° C. Following evolution of hydrogen gas the chloride (1.1 mole) is added to the reaction at room temperature. The reaction is aged for 2-4 hrs. The reaction is quenched when GC analysis indicates less than 10% starting alcohol is present. The reaction mass is washed with 10% aqueous sodium chloride solution. The crude reaction mass is purified by fractional distillation affording the product.

The ethers are synthesized according to the general scheme above with the following specific examples. Equivalents set out are mole equivalents based on starting alcohol, yields are distilled chemical yields based on starting alcohol.

Preparation of Formula III

The 3-methyl oxetanemethanol (1 mole) is dissolved in THF (500 mL) and fed into 60% sodium hydride dispersion (1.1 mole) in THF (500 mL) at 0° C. Following evolution of hydrogen gas the ally chloride (1.1 mole) is added to the reaction at room temperature. The reaction is aged for 2-4 hrs. The reaction is quenched when GC analysis indicates less than 10% starting alcohol is present. The reaction mass is washed with 10% aqueous sodium chloride solution. The crude reaction mass is purified by fractional distillation affording 114 g of 3-allyloxymethyl-3-methyl-oxetane.

Odor: waxy mushroom like.

1.32 ppm (s, 3H) 3.50 ppm (s, 2H) 4.03 ppm (d, 2H, J=5.58 Hz, of t, J=1.43 Hz) 4.36 ppm (d, 2H, J=5.74 Hz) 4.51 ppm (d, 2H, J=5.74 Hz) 5.19 ppm (d, 1H, J=10.41 Hz, of d, J=1.70 Hz 5.28 ppm (d, 1H, J=17.25 Hz, of d, J=1.70 Hz) 5.91 ppm (d, 1H, J=17.24 Hz, of d, J=10.40 Hz, of t, J=5.553 Hz)

Preparation of Formula IV

The 3-methyl oxetanemethanol (1 mole) is dissolved in THF (500 mL) and fed into 60% sodium hydride dispersion (1.1 mole) in THF (500 mL) at 0° C. Following evolution of hydrogen gas the prenyl chloride (1.1 mole) is added to the reaction at room temperature. The reaction is aged for 2-4 hrs. The reaction is quenched when GC analysis indicates less than 10% starting alcohol is present. The reaction mass is washed with 10% aqueous sodium chloride solution. The crude reaction mass is purified by fractional distillation affording 136 g of 3-methyl-3-{[3-methylbut-2-en-1-yloxy]methyl}oxetane.

Odor: floral muguet like.

1.32 ppm (s, 3H) 1.68 ppm (s, 3H) 1.76 ppm (s, 3H) 3.49 ppm (s, 2H) 4.01 ppm (d, 2H, J=6.83 Hz) 4.36 ppm (d, 2H, J=5.74 Hz) 4.49 ppm (d, 2H, J=5.96 Hz) 5.35 ppm (t, 1H, J=6.83 Hz)

Preparation of Formula V

The 3-methyl oxetanemethanol (1 mole) is dissolved in THF (500 mL) and fed into 60% sodium hydride dispersion (1.1 mole) in THF (500 mL) at 0° C. Following evolution of hydrogen gas the prenyl chloride (1.1 mole) is added to the reaction at room temperature. The reaction is aged for 2-4 hrs. The reaction is quenched when GC analysis indicates less than 10% starting alcohol is present. The reaction mass is washed with 10% aqueous sodium chloride solution. The crude reaction mass is purified by fractional distillation affording 190 g of (2E,6E)-3,7-dimethyl-1-[(3-methyloxetan-3-yl)methyloxy]octa-2,6-diene.

Odor: sweet lemon like.

1.32 ppm (s, 3H) 1.61 ppm (s, 3H) 1.68 ppm (2s, 6H) 2.05-2.10 ppm (m, 4H) 3.49 ppm (s, 2H) 4.04 ppm (d, 2H, J=6.70 Hz) 4.36 ppm (d, 2H, J=5.73 Hz) 4.50 ppm (d, 2H, J=5.71 Hz) 5.09 ppm (t, 1H, J=6.81 Hz, of t, J=1.33 Hz) 5.34 ppm (t, 1H, J=6.67 Hz, of d, J=1.19 Hz)

3-{[(2E)-but-2-en-1-yloxy]methyl}-3-methyloxetane

Odor: harsh green octenecarbonate like.

1.32 ppm (s, 3H) 1.8 ppm (s, 2H) 3.48 ppm (s, 2H) 3.96 ppm (d, 2H, J=6.13 Hz) 4.36 ppm (d, 2H, J=5.74 Hz) 4.50 ppm (d, 2H, J=5.73 Hz) 5.54-5.77 ppm (m, 2H)

The following 3-methyl oxetanemethanol ethers are prepared as cited in references provided.

Blaskovich, M; Lajoie, G., J. Amer. Chem. Soc. 115, p5021-30, 1993.

Gorin et al., J. Appl. Chem.USSR, 42, p1095, 1969.

3-methoxymethyl-3-methyl-oxetane

Odor: solvent glue like.

1.31 ppm (s, 3H) 3.40 ppm (s, 3H) 3.45 ppm (s, 2H) 4.35 ppm (d, 2H, J=5.74 Hz) 4.50 ppm (d, 2H, J=5.75 Hz)

3-methyl-3-{[(2-methylprop-2-en-lyl)oxy]methyl}oxetane

Odor: Strong, Green solvent like 1.35 ppm (s, 3H) 1.92 ppm (d, 3H, J=1.32 Hz) 2.18 ppm (d, 3H, J=1.26 Hz) 4.17 ppm (s, 2H) 4.38 ppm (d, 2H, J=5.92 Hz) 4.54 ppm (d, 2H, J=5.93 Hz) 5.73 ppm (t, 1H, J=1.32 Hz)

EXAMPLE 3 PREPARATION OF CARBONATE MATERIALS OF THE PRESENT INVENTION

The following reaction sequence was used to prepare the specific compounds described by the NMR data set forth below:

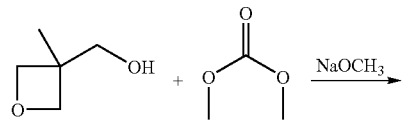

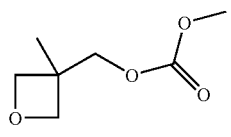

The 3-methyloxetane methanol (1 mole) and dimethylcarbonate (1.5 mole) are combined to which sodium methoxide (0.2 mole) is added. The resulting mixture is heated to 90° C. to 120° C., and methanol is removed from the reaction via a Dean-Stark trap. The reaction is aged until methanol is no longer produced and GC analysis of the reaction indicates less than 10% starting alcohol is present. The reaction mass is cooled to room temperature and neutralized with acetic acid (0.5 mole). The reaction is washed with 10% sodium chloride solution.

The crude reaction mass is purified by fractional distillation affording the product carbonate.

The carbonates are synthesized according to the general scheme above with the following specific examples. Equivalents set out are mole equivalents based on starting alcohol, yields are distilled chemical yields based on starting alcohol.

Ethyl 2-(3-methyloxetane-3-yloxy)acetate 3-methyloxetane methanol 1eq, diethylcarbonate 1.5eq, sodium ethoxide 0.2eq, quench, acetic acid 0.5eq, with 10% sodium chloride solution, yield=85%.

Odor: weak floral.

1.30 ppm (t, 3H, J=7.18 Hz) 1.34 ppm (s, 3H) 4.14 ppm (q, 2H, J=7.14 Hz) 4.17 ppm (s, 2H) 4.25 ppm (d, 2H, J=5.65 Hz) 4.38 ppm (d, 2H, J=5.65 Hz)

Incorporation of 3-methyl-3-{[3-methylbut-2-en-1-yloxy]methyl}oxetane into a fragrance formulation.

A fragrance was prepared according to the following formulation:

| Material | Parts |
|---|---|
| TRIPLAL ® (IFF) | 0.8 |
| Allyl cyclohexyl propionate | 0.5 |
| BORNAFIX ® (IFF) | 10.4 |
| CYCLABUTE ® (IFF) | 9.0 |
| APHERMATE ® (IFF) | 15 |
| Ethyl methyl phenyl glycidate | 1.0 |
| CYCLOGALBANIFF (IFF) | 0.5 |
| Isoamylbutyrate | 1.0 |
| ISOCYCLOCITRAL ® (IFF) | 0.5 |
| JASMAL ® (IFF) | 3.0 |
| Menthone | 0.3 |
| Peach aldehyde | 12.0 |
| 3-methyl-3-{[3-methylbut-2-en-1-yloxy] methyl}oxetane | 5.0 |
| Phenyl acetate | 4.0 |
| HC VERDOX ® (IFF) | 28 |
| FRUCTONE ® (IFF) | 4.0 |

What is claimed is:

1. A compound

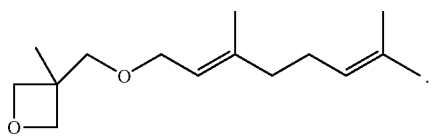

2. A compound

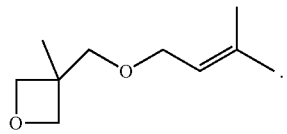

* * * * *